United States Patent [19]

Stutz, Jr.

[11] Patent Number: 5,076,270
[45] Date of Patent: Dec. 31, 1991

[54] APPARATUS AND METHOD FOR MAKING ELECTRICAL CONNECTIONS IN AN IMPLANTABLE PACEMAKER

[75] Inventor: William H. Stutz, Jr., Burbank, Calif.

[73] Assignee: Siemens-Pacesetter, Inc., Sylmar, Calif.

[21] Appl. No.: 649,386

[22] Filed: Jan. 30, 1991

Related U.S. Application Data

[63] Continuation-in-part of Ser. No. 518,618, May 3, 1990, Pat. No. 5,012,807.

[51] Int. Cl.$^5$ .......................................... A61N 1/375
[52] U.S. Cl. .................................................. 128/419 P
[58] Field of Search ...................... 128/419 P, 419 PG

[56] References Cited

U.S. PATENT DOCUMENTS

| | | | |
|---|---|---|---|
| 2,965,734 | 12/1960 | Timmerman | 200/144 |
| 3,571,547 | 3/1971 | Boersma et al. | 200/166 |
| 3,760,332 | 9/1973 | Berkovits et al. | 339/66 R |
| 4,072,154 | 2/1978 | Anderson et al. | 128/419 P |
| 4,182,345 | 1/1980 | Grose | 128/419 P |
| 4,469,104 | 9/1984 | Peers-Trevarton | 128/419 P |
| 4,684,202 | 8/1987 | House et al. | 439/752 |
| 4,712,557 | 12/1987 | Harris | 128/419 P |
| 4,715,380 | 12/1987 | Harris | 128/419 P |
| 4,764,132 | 8/1988 | Stutz | 439/810 |
| 4,848,346 | 7/1989 | Crawford | 128/419 P |
| 4,934,366 | 6/1990 | Truex et al. | 128/419 P |
| 5,012,807 | 5/1991 | Stutz, Jr. | 128/419 X |

FOREIGN PATENT DOCUMENTS

| | | |
|---|---|---|
| 0052879 | 6/1982 | European Pat. Off. . |
| 2383532 | 10/1978 | France . |
| 29822 | of 1914 | United Kingdom . |

OTHER PUBLICATIONS

Calfee et al., "A Voluntary Standard for 3.2 mm Unipolar and Bipolar Pacemaker Leads and Connectors", Pace, vol. 9, pp. 1181-1185 (Nov.-Dec. 1986, Part II).

Primary Examiner—William E. Kamm
Attorney, Agent, or Firm—Lisa P. Weinberg; Malcolm J. Romano

[57] ABSTRACT

A multi-part molded pacemaker connector that meets the precise requirements imposed by the VS-1 standard, yet does not require complex or expensive machining of individual parts. Advantageously, the pacemaker connector is made from a plurality of individually molded parts, with each individual part being designed to readily allow the insertion of seals and other connector components, prior to joining the parts together. The connector includes three molded pieces: a body tip, a body ring, and an entrance connector which are adapted to be joined during assembly. The connector further includes a garter spring, and preferably, two annular sealing rings. A tip connector block is insert-molded into the body tip. A conductive tube, which forms the ring connector, is insert-molded within the entrance connector. The body ring provides appropriate spacing between the tip connector block and the ring connector. Windows in the body tip and the body ring expose a portion of the conductor block and the conductive tube, respectively, for subsequent attachment to conductive wires. After assembly, the connector may be pretested for leakage, dimensionality and conductivity prior to casting it in epoxy as part of the pacemaker connector.

24 Claims, 5 Drawing Sheets

APPARATUS AND METHOD FOR MAKING ELECTRICAL CONNECTIONS IN AN IMPLANTABLE PACEMAKER

CROSS-REFERENCE TO RELATED PATENT APPLICATIONS

This is a continuation-in-part of the prior application Ser. No. 07/518,618, filed 5/3/90 now U.S. Pat. No. 5,012,807.

BACKGROUND OF THE INVENTION

The present invention relates to implantable pacemakers, and more particularly to a connector used by an implantable pacemaker that allows a pacing lead to be detachably, yet reliably, connected to the pacemaker. Even more particularly, the present invention relates to a pacemaker connector made in compliance with precise industry imposed standards, but made in a way that does not require expensive, precision parts, nor a complex assembly or manufacture.

A pacemaker is a medical device that selectively provides stimulation pulses to the heart, or other body tissue, for the purpose of causing a desired muscle contraction. When properly used, a pacemaker can maintain a desired heart rate, causing the heart to beat so as to maintain the efficient flow of blood through a patient's body.

Modern pacemakers are made to be implanted in a patient, typically in a "pocket" of fatty tissue near the patient's upper breast or lower abdomen. As such, the electronic circuits used within a pacemaker are hermetically sealed in a suitable housing, compatible with body tissue. Electrical connection is made with the pacemaker circuits via feedthrough terminals that pass through the hermetically sealed housing. These feedthrough terminals are then electrically connected to a "pacemaker connector", which pacemaker connector is attached to the pacemaker housing. A pacemaker lead is used with an implantable pacemaker in order to maintain electrical contact between a desired tissue location and the pacemaker circuits. For cardiac pacing, such lead is typically inserted through one of the main veins of the patient, e.g., the superior vena cava, so that a distal end of the lead is directed inside of the heart. Electrodes positioned at the distal end of the lead make contact with the cardiac tissue. The proximal end of the pacemaker lead is then connected to the pacemaker connector.

The pacemaker connector typically takes the form of a female connector, with the proximal end of the pacemaker lead taking the form of a male connector. When joined together, good electrical contact must be maintained between a proximal electrode of the pacemaker lead and an appropriate feedthrough terminal of the pacemaker housing. Further, such connection must be secure, so that it does not disconnect during use, yet it must be detachable, in the event the pacemaker or lead needs to be replaced. Moreover, such connections must at all times remain insulated and sealed from body fluids, which body fluids are conductive and could cause an electrical short.

For single conductor pacemaker leads, the pacemaker connector has typically included a connector block having a recess or hole into which a proximal electrode pin of the pacing lead is inserted and secured with a set screw. Suitable means are then used to electrically connect the connector block to the pacemaker's feedthrough terminal. The connector block is then cast into a suitable epoxy "header assembly" that forms the "connector top" portion of the pacemaker. The cast header assembly both insulates the connector block from body fluids, and positions the header block so as to properly receive the proximal electrode of the pacemaker lead. For multi-conductor pacemaker leads, e.g., bipolar pacing leads, one or more proximal ring electrodes of the pacing lead must also make secure electrical contact with an appropriate feedthrough terminal on the pacemaker housing. Numerous schemes have been proposed and used over the years to achieve this purpose, with varying degrees of success. See, e.g., U.S. Pat. No. 4,764,132 (an earlier patent of Applicant's directed to the problem of making a secure electrical connection to the delicate proximal ring electrode of a pacing lead using a set screw without deforming the proximal ring electrode).

Thus, over the approximately 30 year history of implantable pacemakers, a wide variety of techniques and methods have been used to connect leads to pacemakers. Many of these methods and techniques are no longer suitable for the smaller pacemakers and leads that are currently being used.

Recently, an effort has been underway to standardize the interface between a pacemaker lead and a pacemaker. See, e.g., Calfee et al., "A Voluntary Standard for 3.2 mm Unipolar and Bipolar Pacemaker Leads and Connectors," PACE, Vol. 9, 1181-85 (Nov.-Dec. 1986). The standard therein proposed, referred to as the VS-1 (voluntary standard-1), has subsequently been adopted by almost all pacemaker manufacturers worldwide. The VS-1 standard does not specify how a particular pacemaker connector must make contact with a pacemaker lead, it simply defines the dimensions of the pacemaker lead and the dimensions of the pacemaker connector cavity into which the pacemaker lead is inserted. The VS-1 standard further specifies certain requirements as to leakage, conductivity and connection/disconnection force. While the VS-1 standard advantageously represents a long needed movement towards industry standardization, when translated to a particular type of pacemaker connector design, the VS-1 standard disadvantageously sets some rather stringent manufacturing tolerances. Such stringent manufacturing tolerances have heretofore only been obtainable using labor intensive, expensive manufacturing techniques, e.g., machining of individual parts.

What is needed, therefore, is a pacemaker connector that meets the VS-1 standard, and that also can be made using less labor-intensive and less expensive manufacturing methods and techniques. The present invention advantageously addresses this and other needs.

SUMMARY OF THE INVENTION

In accordance with one aspect of the present invention, there is provided a pacemaker connector that meets the precise requirements imposed by the VS-1 standard (or any other applicable standard), yet that does not require complex nor expensive machining of individual parts. Advantageously, the pacemaker connector of the present invention is made from a plurality of individually molded parts, with each individual part being designed to readily allow the insertion of seals and other connector components, prior to joining the parts together. That is, the present invention provides a pacemaker connector design which facilitates its assembly.

The present invention includes three molded parts: a body tip, a body ring, and an entrance connector. The body tip is molded to include a conductive connector block having a channel therethrough for receiving the proximal tip electrode of the pacemaker lead. The body tip includes at least one "window" in the molded plastic that exposes a portion of the conductor block for subsequent attachment of a first conductor. The first conductor is used to provide electrical connection between the conductor block and a pacemaker feedthrough terminal.

The entrance connector is molded to include a conductive tube which extends out one end of the entrance connector. The conductive tube acts like a second conductor block. The entrance connector includes a recess at the other end for receiving a sealing ring therein. A garter spring contact is inserted within the entrance connector so as to make circumferential contact with an inner surface of the conductive tube. The entrance connector further has a shoulder for retaining the garter spring contact and preventing it from moving axially within the entrance connector.

The body ring is molded to include a channel at one end for receiving the conductive tube, a second recess at the opposite end for receiving a second sealing ring therein, and a channel therethrough for passing the proximal ring electrode of a pacemaker lead. The body ring also has at least one window in the molded plastic. Once the entrance connector is joined with the body ring, the window provides access to the conductive tube for attachment of a second conductor. The second conductor provides electrical connection between the conductive tube and a second pacemaker feedthrough terminal. A shoulder within the body ring prevents the garter spring contact from moving axially off of the exposed conductor tube. The sealing rings are adapted to provide a tight seal around a pacemaker lead when inserted into the connector. The body ring is then joined to the body tip at one end and to the entrance connector at the other end, to form the completed pacemaker connector assembly.

Advantageously, after assembly of the pacemaker connector (i.e., after joining the body ring to the body tip and the entrance connector), the pacemaker connector may be pretested for leakage, dimensionality and conductivity. If these tests are successfully passed, then the first and second conductors are welded, or otherwise bonded, from the conductor block and the conductive tubing to the appropriate feedthrough terminals of a hermetically sealed pacemaker housing (pacemaker "can"). In the preferred embodiment, the first and second conductors are advantageously realized by simply welding or otherwise securing ribbon conductors to the first and second pacemaker terminals. The pacemaker connector and ribbon conductors are then cast in epoxy, or equivalent, and are thus bonded to the pacemaker housing to form a pacemaker header assembly as part of the final pacemaker assembly.

The present invention advantageously allows first and second spaced apart proximal electrodes of a pacemaker lead to be inserted into the pacemaker connector and make respective electrical contact with the connector block by way of a set screw connection and with the conductive tubing by way of a garter spring contact, thereby allowing electrical contact to be made with the first and second proximal electrodes of the pacing lead via the ribbon conductors.

The present invention further contemplates a method of making a molded pacemaker connector comprising the steps of: "insert molding" a connector block into a tip connector mold; "injection molding" a ring connector; "insert molding" a conductive tube into an entrance connector mold; allowing the polymers to cure; and removing the cured polymers from the connector molds to yield a molded body tip, a body ring, and an entrance connector, respectively. The method further contemplates inserting a first sealing ring into one end of the body ring and a second sealing ring into one end of the entrance connector; and inserting a garter spring contact into the other end of the molded entrance connector so as to make physical contact with an inner surface of the conductive tube. Next, the method includes joining the tip connector to one end of the ring connector, and joining the entrance connector to the other end of the ring connector.

It is thus a feature of the present invention to provide a pacemaker connector, and method of making a pacemaker connector, that meets the VS-1 standard or any other standards that may be imposed, such as the proposed ISO DIS 5841-3 standard, presently under consideration by the Food and Drug Administration.

It is a further feature of the invention to provide such a connector that is easy and inexpensive to manufacture and assemble, avoiding the necessity of machining individual parts in order to obtain precision dimensions.

It is another feature of the invention to provide such a pacemaker connector that may be used with either pacemaker leads having seals (VS-1B) or not having seals.

It is still another feature of the invention to provide such a pacemaker connector that can be pretested for leakage, conductivity and dimensionality prior to being cast into a pacemaker header assembly.

It is yet another feature of the invention to provide a pacemaker connector utilizing a "canted coil garter spring contact" to make electrical contact around the entire periphery of a proximal electrode, e.g., a proximal ring electrode, of a pacemaker lead, thereby maintaining a safe, reliable and secure electrical connection.

It is a further feature of the invention to provide a simple method of making a multi-part pacemaker connector that assures a leak-tight press-fit between the individual components thereof.

Finally, all of the aforesaid advantages and objectives are achieved without incurring any substantial relative disadvantage. It will therefore be perceived that the advantages of the present invention result in a multi-part pacemaker connector designed to readily allow the insertion of seals and other connector components prior to joining the parts together, which is an easy and inexpensive way to manufacture, while avoiding the necessity of machining individual parts in order to obtain precise dimensions, thus, making the method of the present invention a highly desirable enhancement to implantable cardiac pacemaker therapy.

BRIEF DESCRIPTION OF THE DRAWINGS

The above and other features and advantages of the present invention will be more apparent from the following more particular description thereof presented in conjunction with the following drawings wherein.

DETAILED DESCRIPTION OF THE INVENTION

The following description presents the best mode contemplated for practicing the invention. This description is not to be taken in a limiting sense but is made merely for the purpose of describing the general principles of the invention. The scope of the invention should be ascertained with reference to the claims. The present invention will be explained with reference to the above-described figures, wherein like numerals are used to represent like parts or elements throughout.

Figure 1:
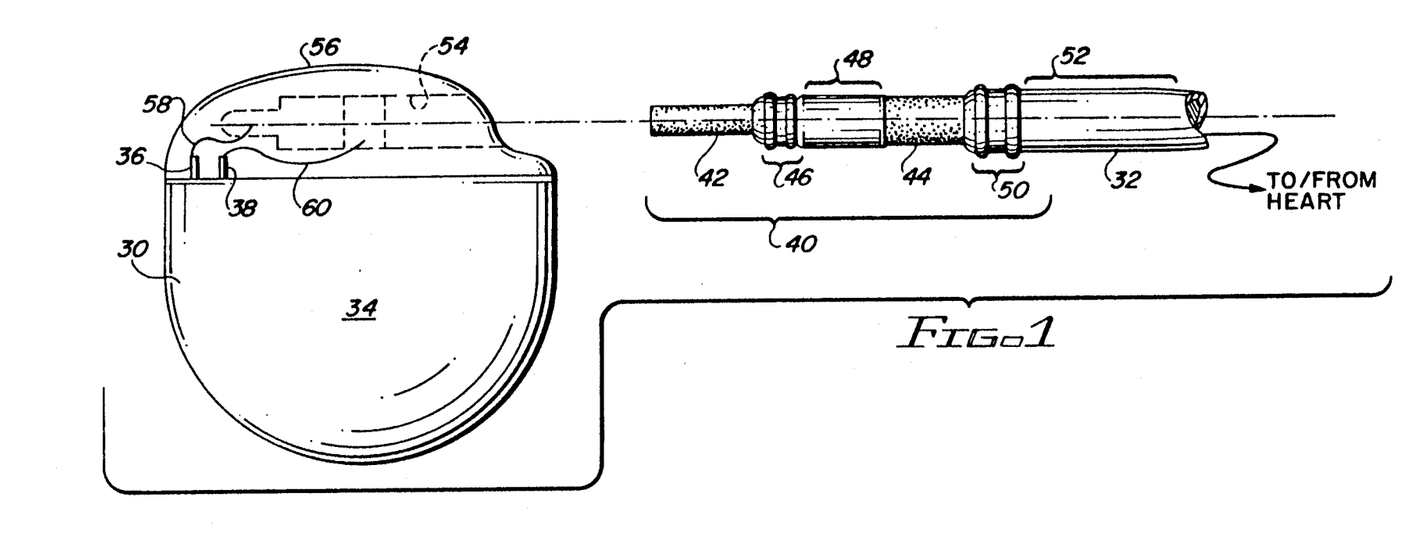
FIG. 1 diagrammatically depicts the main elements of a pacemaker system, including a pacemaker and a side profile view of the proximal end of a pacemaker lead adapted to be inserted into the pacemaker connector.

In FIG. 1 there is shown a diagram of the main elements of a pacemaker system, including a pacemaker 30 and a pacemaker lead 32. The pacemaker 30 includes a hermetically sealed housing or (as it is more frequently referred to as) pacemaker "can" 34, inside of which the pacemaker electronic circuits and battery are housed. Electrical contact between the electronic circuits and the pacemaker lead is made with by means of one or more feedthrough terminals 36, 38. In some models of pacemakers, the pacemaker can 34 is made from an electrically conductive material, and electrical contact may also be made through an exposed (non-insulated) portion of the conductive material of the pacemaker can 34.

FIG. 1 illustrates a proximal end 40 of a bipolar pacemaker lead 32 made in accordance with the VS-1 standard. This side profile of the proximal end 40 includes a proximal tip electrode 42 and a proximal ring electrode 44. Adjacent to the tip electrode 42 is a first set of sealing rings 46, followed by a smooth portion 48. Adjacent to the ring electrode 44 is a second set of sealing rings 50, followed by a smooth portion 52. The tip electrode 42 and the ring electrode 44 make respective electrical contact with the feedthrough terminals 36, 38 of the pacemaker 30 by way of a pacemaker connector 54. The outline of pacemaker connector 54 is shown in FIG. 1 as a dotted line within a pacemaker header assembly 56.

The pacemaker connector 54, explained in more detail below, is formed within the header assembly 56 so as to receive the proximal end 40 of the pacemaker lead 32. The header assembly 56, in turn, is fastened to the top of the pacemaker can 34. A first conductor 58 and a second conductor 60 are included in the header assembly 56 for making electrical contact between appropriate terminals of the pacemaker connector 54 and the feedthrough terminals 36, 38.

In use, the proximal end 40, functioning as a "male" connector, slides inside of the pacemaker connector 54, functioning as a "female" connector. It is the function of the pacemaker connector 54 to allow a reliable, yet detachable, electrical contact to be maintained between the tip and ring electrodes 42, 44 and the respective feedthrough terminals 36, 38.

It is noted that the pacemaker connector 54 invention described herein is described in terms of a bipolar connection. That is, the invention is described with reference to the use of a bipolar pacemaker lead, i.e., a pacemaker lead having two separate conductors, one connected to a proximal tip electrode and the other connected to a proximal ring electrode. However, it is to be understood that various aspects of the invention also have applicability to unipolar pacing (single conductor leads), or multi-polar pacing (multiple conductor leads).

Figure 2:
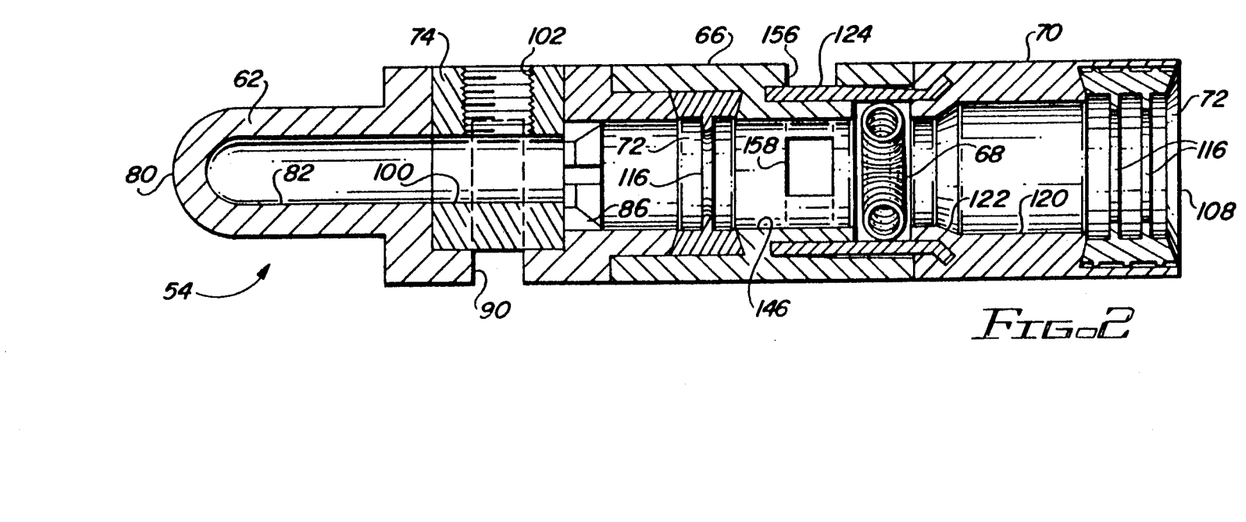
FIG. 2 is a profile cross-sectional view of a preferred embodiment of an assembled multi-part molded pacemaker connector made in accordance with the present invention.

As shown in FIG. 2, a cross-sectional view of a preferred embodiment of a multi-part molded pacemaker connector made in accordance with the present invention is designated generally by the reference numeral 54. The individual components of the pacemaker connector 54 are best seen in the exploded view of the pacemaker connector shown in FIG. 3. However, many of the details associated with these components, as well as their manner of assembly, can also be ascertained from the other figures. Hence, in the discussion that follows, reference should be made to whichever figure(s) best depicts the particular element(s) being described. The same numerals will be used to describe the same parts throughout.

Figure 3:
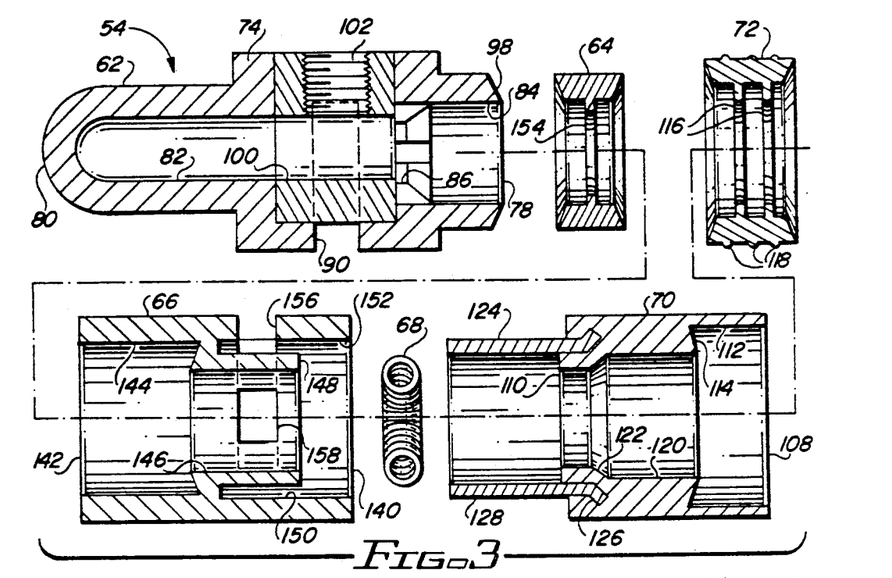
FIG. 3 is an exploded view of the multi-part molded pacemaker connector shown in FIG. 2A.

As shown in FIG. 3, the components of the pacemaker connector 54 include a body tip 62, a first inner seal 64, a body ring 66, a garter spring contact 68, an entrance connector 70, and a second inner seal 72. The body tip 62, body ring 66 and the entrance connector 70 are molded parts which readily allow the insertion of the inner seals 64, 72 and the garter spring contact 68 prior to them being joined together, thereby facilitating their manufacturability. The body ring 66 and entrance connector 70 have a main channel or opening through which the proximal end 40 of the pacemaker lead 32 passes or enters when inserted into the pacemaker connector 54. The body tip 62 also has a main channel or opening into which the proximal end 40 of the pacemaker lead 32 resides when it is inserted into the pacemaker connector 54.

Figure 4A:
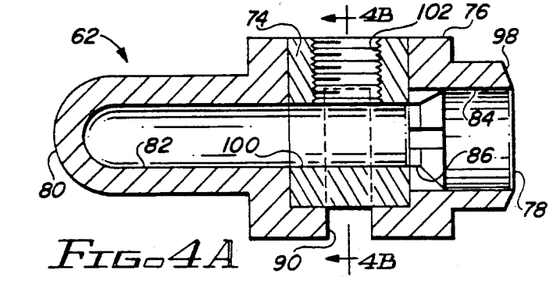
FIG. 4A is a profile cross-sectional view of the molded body tip, including the conductor block, of the multi-part molded pacemaker connector shown in FIG. 2A.
Figure 4B:
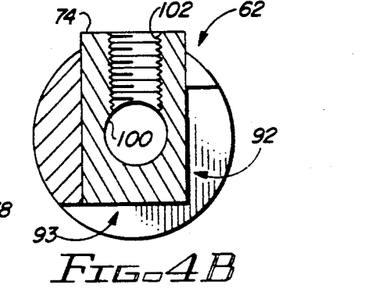
FIG. 4B is a cross-sectional view of the body tip of the multi-part molded pacemaker connector shown in FIG. 4A.
Figure 4C:
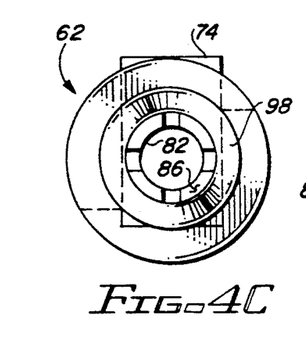
FIG. 4C is an end view of the body tip of the multi-part molded pacemaker connector shown in FIG. 4A as viewed from the open end.
Figure 4D:
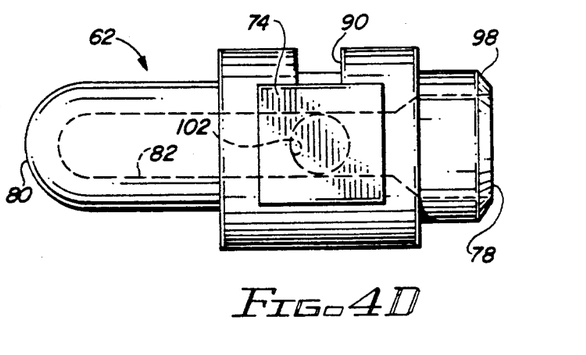
FIG. 4D is a top view of the body tip of the multi-part molded pacemaker connector shown in FIG. 4A.
Figures 4E, 5A, 5B:
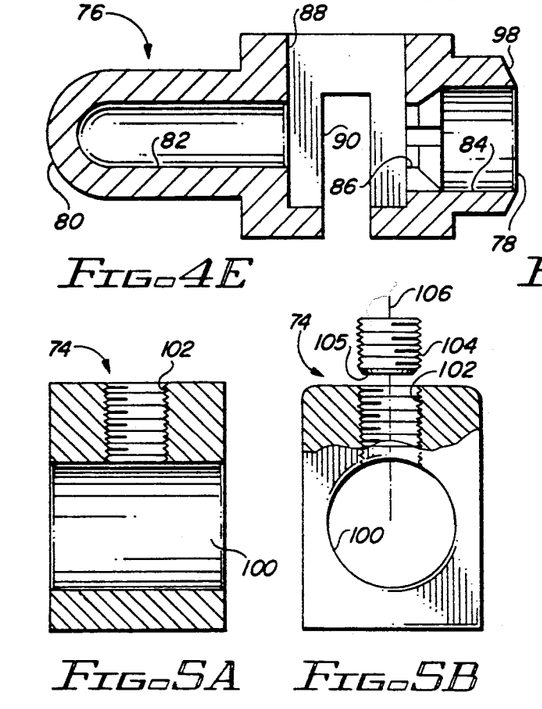
FIG. 4E is a profile cross-sectional view of the body tip without the conductor block molded therein.
FIG. 5A is a profile cross-sectional view of the conductor block used in the body tip shown in FIG. 4A.
FIG. 5B is a partial cross-sectional view of the conductor block, including the set screw.

Several additional views of the body tip 62 are shown in FIGS. 4A, 4B, 4C, 4D, 4E, and 4F. FIG. 4A shows a cross-sectional profile view of the body tip 62, including a conductor block 74 molded therein. FIG. 4B shows a cross-sectional view of the body tip 62 across the lines B—B. FIG. 4C shows a view of the body tip 62 from an open end 78. FIG. 4D shows a top view of the body tip 62 and the conductor block 74. FIG. 4E shows just the polymer tip portion 76 of the body tip 76 without the conductor block 74.

As best seen in FIG. 4E, the body tip 62 includes a tubular shaped, polymer tip portion 76. The polymer tip portion 76 has an open end 78 and a closed end 80. The closed end 80 provides a channel 82 where a portion of the tip electrode 42 of the pacemaker lead 32 may reside. A recess 84 at the open end 78 of the polymer tip portion 76 provides a smooth inner surface against which the sealing rings 46 (FIG. 1) of the proximal end 40 of the pacemaker lead 32 may act to form a fluid-tight seal. A narrow neck 86 defines a diameter that is just large enough for the tip electrode 42 to pass therethrough, but sufficiently small to prevent the sealing rings 46 (FIG. 1) from passing therethrough.

Figure 4F:
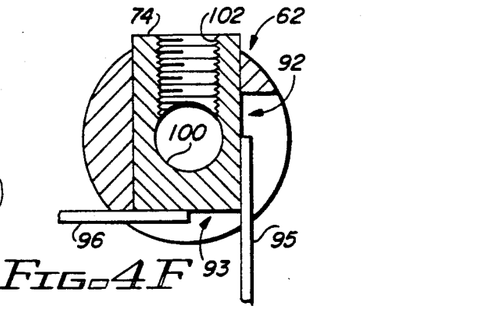
FIG. 4F is the cross-sectional view of the body tip shown in FIG. 4A, which details the attachment of two ribbon conductors from two different vantage points.

As shown in FIG. 4E, a cavity 88 in the polymer tip portion 76 identifies the location where the conductor block 74 is "insert molded" therein. Insert molding is simply the process in which components are inserted into a mold and cured together with the injected polymer. In the preferred embodiment, the polymer used is polysulfone. A window 90 is molded therein to expose a portion of the conductor block 74 for the attachment of the first conductor 58 (FIG. 1). The window 90 exposes two sides 92 and 93 (FIG. 4B) of the conductor block 74 to facilitate a convenient attachment of the first conductor 58 from two different possible positions 95, 96 as shown in FIG. 4F. A circumferential protruding shoulder 98 provides a surface or stub that is press-fittably inserted into the body ring 66 when the body ring 66 is joined to the body tip 62. The front edge of the shoulder 98 is angled (e.g., chamfered at 15 degrees), the reason for which will be described below in conjunction with the description of the body ring 66.

Figure 5C:
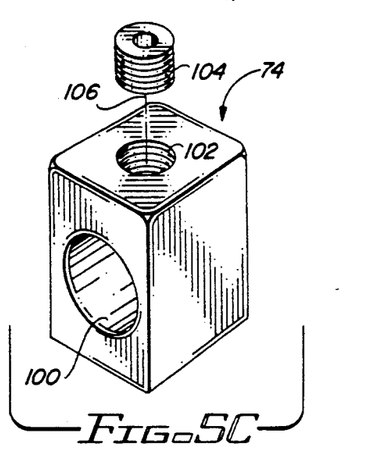
FIG. 5C is a perspective view of the conductor block and the set screw.

As shown in FIGS. 4A and 4D, a conductor block 74 is molded into the body tip 62 so as to form an integral part thereof. As best seen in FIGS. 5A, 5B, and 5C, the connector block is a square conductive piece which has a hole or channel 100 drilled therethrough. The tip electrode 42 is received in the channel 100 when the proximal end 40 of the pacemaker lead 32 is inserted into the pacemaker connector 54. Another hole or channel 102, transverse to the channel 100, is threaded so as to receive a set screw 104. Hence, when the tip electrode 42 is inserted into the channel 100, the set screw 104 may be urged along the movement axis 106 in a conventional manner in order to firmly secure the tip electrode 42 to the conductor block 74 and to secure the pacemaker lead 32 in place axially. The set screw 104 has a flat end 105 to prevent damage to the lead 32 when the set screw 104 is urged along the movement axis 106. The conductor block 74 is preferably made from a conductive material compatible with body fluids such as 316L stainless steel. In the present invention, the conductor block 74 is precisely seated in the appropriate mold cavity for the body tip 62. The injection molding process is then carried out in conventional manner. As the polysulfone (or other equivalent material) cures, the connector block 74 is permanently held in its prescribed position within the body tip 62.

It is noted that other means may be used to secure the tip electrode 42 within the pacemaker connector 54 other than the conventional set screw 104 and connector block 74 configuration described above. For example, a set-screwless connection scheme may be employed using two garter spring contacts, one for contacting the tip electrode 42, the other for contacting the ring electrode 44. However, if this two spring arrangement is used, an additional axial retention means for the pacemaker lead 32 is required to prevent possible disconnection. For a complete description of a set-screwless connection scheme, see U.S. Pat. No. 4,934,366, which patent is assigned to the same assignee as the present application. U.S. Pat. No. 4,934,366 is hereby incorporated herein by reference.

Figure 6A:
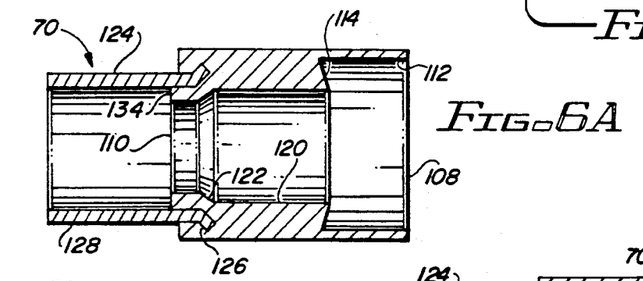
FIG. 6A is a profile cross-sectional view of the molded entrance connector, including the conductive tube, of the multi-part molded pacemaker connector shown in FIG. 2A.
Figure 6B:
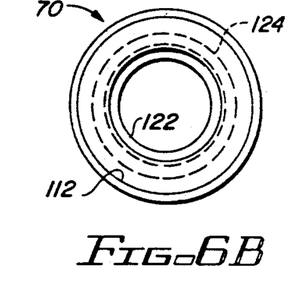
FIG. 6B is an end view of the entrance connector subassembly of the pacemaker connector shown in FIG. 6A.
Figure 7A:
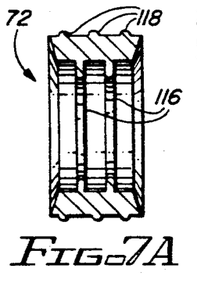
FIG. 7A is a profile cross-sectional view of the second inner seal.
Figure 7B:
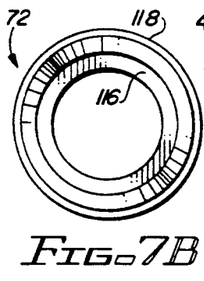
FIG. 7B is a cross-sectional view of the second inner seal.

As best seen in FIGS. 6A and 6B, the entrance connector 70 is a tubular molded part having an open front end 108 and an open rearward end 110. At the front end 108 of the entrance connector 70 is a first recess 112. This recess 112 is dovetailed, as shown at 114. This first dovetailed recess 112 is designed to receive the second inner seal 72 (FIG. 3). The recess 112 holds the second inner seal 72 captive in such a way that it cannot be dislodged by insertion or extraction of a lead. The second inner seal 72, which is sometimes referred to as an entrance seal, is shaped like a ring or doughnut, as shown in FIGS. 7A and 7B. The second inner seal 72 is shown to have inner circumferential ridges 116 adapted to make sealing contact with the smooth surface 52 (FIG. 1) of the pacemaker lead 32. The second inner seal 72 also has outer circumferential ridges 118 adapted to make sealing contact with the smooth inner diameter of the recess 112.

In FIG. 6A, the entrance connector 70 has a second recess 120. This second recess 120 is adjacent to the dovetailed recess 112, having a smaller diameter than the recess 112. It is the function of the second recess 120 to provide a smooth surface against which the sealing rings 50 (FIG. 1) of the pacemaker lead 32 may make sealing contact. (Note from the cross-sectional view of FIG. 6A that the recesses have the appearance of counterbores having differing diameters. However, because the use of the term "counterbore" could imply that the counterbore is machined into the particular part wherein the counterbore is found, and whereas the recesses and are not machined, but are formed during the molding process of the body tip 62, the term "counterbore" is not used herein.)

Moving rearward through the entrance connector 70 (i.e., right-to-left as drawn in FIG. 6A), there is next found a narrow neck 122. The narrow neck 122 defines a diameter that is just large enough for the ring electrode 44 to pass therethrough, but sufficiently small to prevent the sealing rings 50 (FIG. 1) of the pacemaker lead 32 from passing therethrough. A conductive tube 124 has a flanged portion 126 at one end for retention purposes. The flanged portion 126 of the conductive tube 124 is "insert molded" into the rearward end 110 of the entrance connector 70 so as to make it an integral part thereof. A non-flanged portion 128 of the conductive tube 124 extends outwardly from the rearward end 110 of the entrance connector 70. The conductive tube 124 is preferably made of 316L stainless steel. As the polysulfone (or other equivalent material) cures, the conductive tube 124 is permanently held in its prescribed position within the entrance connector 70.

Figure 6C:
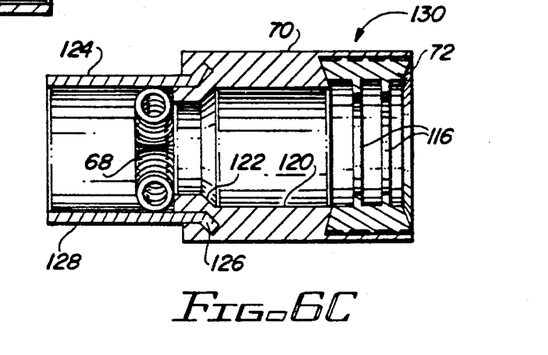
FIG. 6C is a profile cross-sectional view of the entrance connector subassembly of the pacemaker connector shown in FIG. 2A, wherein the entrance connector subassembly includes the molded entrance connector, the second inner seal, the conductive tube, and the garter spring.
Figures 8A, 8B:
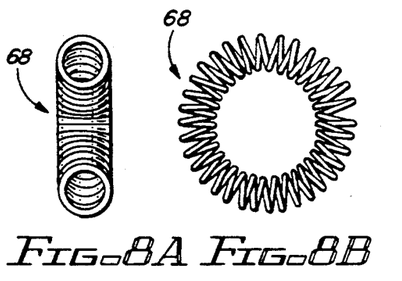
FIG. 8A is a profile cross-sectional view of the garter spring contact.
FIG. 8B is a cross-sectional view of the garter spring contact.

In FIG. 6C, an entrance connector subassembly 130 is shown. The entrance connector subassembly 130 includes the garter spring contact 68 (FIG. 3). (Cross-sectional views of the garter spring contact 68 are also shown in FIGS. 8A and 8B.) The garter spring contact 68 is inserted into the conductive tube 124 so that it makes circumferential contact with the inner surface of the conductive tube 124 and rests against a shoulder 134 (FIG. 6A) in the entrance connector 70. A suitable garter spring contact 68 may be obtained commercially from Bal Seal Engineering Company, Inc., of Santa Ana, Calif., and is also known as a "canted coil" spring, or a "canted coil garter spring contact". The dimensions of the garter spring contact 68 are such that its inner diameter protrudes into the channel formed by the conductive tube 124. The inner diameter of the garter spring contact 68 is a slightly smaller diameter than the outer diameter of the ring electrode 44. Hence, when the proximal end 40 of the pacemaker lead 32 is inserted into the pacemaker connector 54, the ring electrode 44 compresses the garter spring contact 68 somewhat in order to expand its diameter to allow the ring electrode 44 to fit therein. This compression advantageously assures that the garter spring contact 68 surrounds and makes good multi-point electrical contact around the entire circumference of the ring electrode 44. At this same time, this compression also assures that the outer diameter surface of the garter spring contact 68 is pushed against and makes good multi-point electrical contact with the entire inner circumference of the conductive tube 124. Of course, the garter spring contact 68 is inserted into the entrance connector 70 prior to joining the body ring 66 to the entrance connector 70, thereby facilitating assembly of the pacemaker connector 54. Thus, the entrance connector subassembly 130 shown in FIG. 6C includes the molded entrance connector 70, the conductive tube 124, the garter spring contact 68 and the second inner seal 72.

Figure 9A:
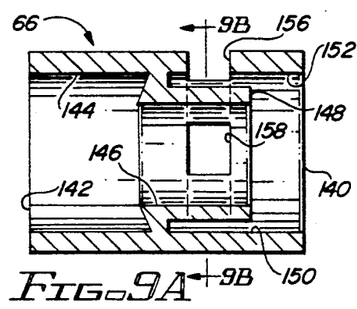
FIG. 9A is a profile cross-sectional view of the molded body ring of the multi-part molded pacemaker connector shown in FIG. 2A.
Figure 9B:
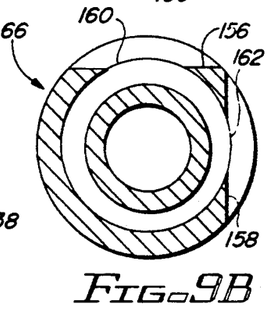
FIG. 9B is an end view of the body ring portion shown in FIG. 9A.

As shown in FIG. 9A and 9B, the body ring 66 is a tubular molded part which has an open front open 140 and an open rearward end 142. At the rearward end 142 of the body ring 66, there is a recess 144. The recess 144 is dimensioned so as to provide a leak-proof fit when the body tip 62 and the body ring 66 are joined, with the shoulder 98 (FIG. 4A) of the body tip 62 tightly fitting within the recess 144 of the body ring 66. The recess 144, when mated with the shoulder 98, forms a dovetail recess for receiving the first inner seal 64 (FIG. 3). The recess 144 holds the first inner seal 64 captive in such a way that it cannot be dislodged by insertion or extraction of a lead.

Figure 9C:
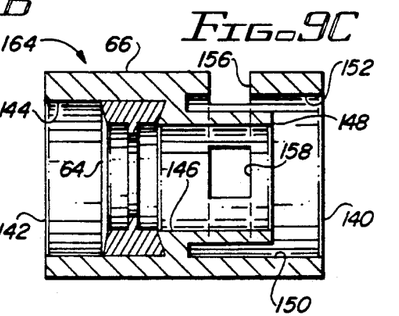
FIG. 9C is a profile cross-sectional view of the molded body ring subassembly of the multi-part molded pacemaker connector shown in FIG. 2A, the subassembly including the body ring and the first inner seal.

A recess 146, adjacent to the recess 144, defines a diameter that is just large enough for the ring electrode 44 to pass therethrough. The recess 146 also forms a shoulder 148 and a channel 150. The shoulder 148 is used to prevent lateral movement of the garter spring contact 68 in a rearward direction when the body ring 66 is joined with the entrance connector subassembly 130. The channel 150 is used to receive the conductive tube 124 which is molded in the entrance connector 70. The recess 146 is also adjacent to a larger recess 152 at the front end 140 of the body ring 66. Recess 152 is dimensioned so as to provide a leak-proof fit when the body ring 66 and the entrance connector 70 are joined, with the shoulder 148 of the body ring 66 tightly fitting against the conductive tube 124 of the entrance connector 70. The body ring subassembly 164, including the body ring 66 and the first inner seal 64, is shown in FIG. 9C.

Figure 10A:
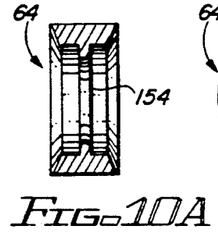
FIG. 10A is a profile cross-sectional view of the first inner seal.
Figure 10B:
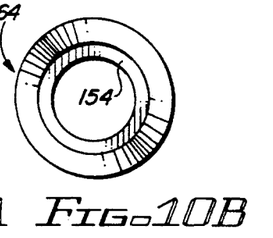
FIG. 10B is a cross-sectional view of the first inner seal.

Details of the first inner seal 64 are shown in FIG. 10A and 10B. The first inner seal 64 has one or two inwardly protruding sealing rings 154 adapted to make sealing contact with the smooth surface 48 of the pacemaker lead 32 when the proximal end 40 of the pacemaker lead 32 is inserted into the pacemaker connector 54. Of course, the first inner seal 64 is inserted into the body ring 66 prior to joining the body ring 66 to the body tip 62, thereby facilitating assembly of the pacemaker connector 54.

As best seen in FIG. 9A and 9B, the molded body ring 66 includes a first and second window 156, 158 therethrough to provide access to the conductive tube 124. In the preferred embodiment, two windows are used to facilitate a convenient attachment of the second conductor 60 from two different possible contact points 160, 162 on the conductive tube 124. In the embodiment shown in FIG. 11, the access windows chosen are located on one side of the pacemaker connector 54. However, it is understood that the access windows for the body tip 62 and body ring 66 may be any point which is convenient for attaching the conductors without departing from the spirit of the invention.

After the body tip 62 (FIG. 4A), the body ring subassembly 164 (FIG. 5C), and the entrance connector subassembly 130 (FIG. 6C) have been joined to produce the completed pacemaker connector 54 (shown in FIG. 2A), the pacemaker connector 54 can be pretested for leakage, dimensionality, conductivity, as well as for any other specified parameters, such as proper lead insertion/removal forces. This ability to pretest the pacemaker connector 54 significantly improves the yield of the overall pacemaker manufacturing process. Further, the multi-part nature of the pacemaker connector allows the pacemaker connector to be inexpensively manufactured or reworked, if required.

Once the pacemaker connector 54 has been assembled (FIG. 2) and tested as described above, the first and second conductors 58, 60 (FIG. 1) are attached to the pacemaker connector 54. The first conductor 58 is attached to the conductor block 74 through the access windows 90 on either side 92 or 93 (FIG. 4F) of the conductor block 74. The second conductor 60 is attached to the conductive tube 124 through either one of the access windows 156 or 158 (FIG. 9B) in the body ring 66.

Figure 11:
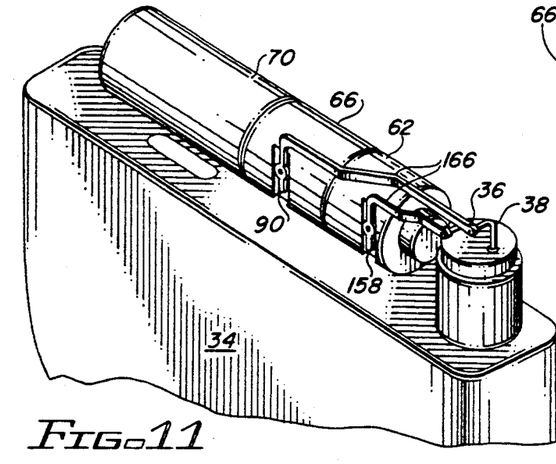
FIG. 11 is a perspective view of the multi-part molded pacemaker connector, with ribbon conductors welded into place, just prior to casting the epoxy header assembly.

In the preferred embodiment, electrical contact is made by welding or otherwise attaching a preformed conductor ribbon set 166, as shown in FIG. 11. The ribbon conductor set 166 is formed by chemical etching and/or forming a thin sheet of conductive material to define a plurality of conductor ribbons supported within a frame (not shown). The ribbon conductor set 166 and frame are shaped in a predetermined precise array to extend between the conductor blocks and the feedthrough terminals 36, 38. After welding, the frame is removed. For a complete description of the ribbon conductor set, reference is made to copending U.S. patent application Ser. No. 07/439,070, filed on 11/20/89, which patent application is assigned to the same assignee as is the present invention. U.S. patent application Ser. No. 07/439,070 is hereby incorporated herein by reference.

Once the ribbon conductor set 166 is attached to the pacemaker connector 54, the pacemaker connector 54 is then properly positioned above the pacemaker can 34 (using an appropriate header assembly mold or fixture guide), and the conductor ribbon set 166 is positioned appropriately so as to make electrical contact with the feedthrough terminals 36, 38. In so doing, care must be exercised to make sure the conductor ribbons 166 do not touch each other. Preferably, the ends of the conductor ribbons 166 are welded, or otherwise permanently bonded, to the feedthrough terminals 36, 38. Once so attached, the pacemaker header assembly 56 (FIG. 1) is completed by casting the pacemaker connector 54 in a biocompatible epoxy, such as Hysol, which epoxy also serves to bond the header assembly 56 to the pacemaker can 34.

It is noted that the inner seals 64, 72 are preferably made from a flexible silicon elastomer, having a 70A shore hardness. The conductor ribbon set 166 is preferably made from 316L stainless steel. The garter spring contact 68 is made from a suitable corrosion-resistant conductive spring material, such as MP35N alloy.

The dimensions for the pacemaker connector 54, including the component parts used therein, are dictated by the particular connector standard, or other connector specification, that is used. The VS-1. dimensions, for example, are published in the known literature.

Figure 12:
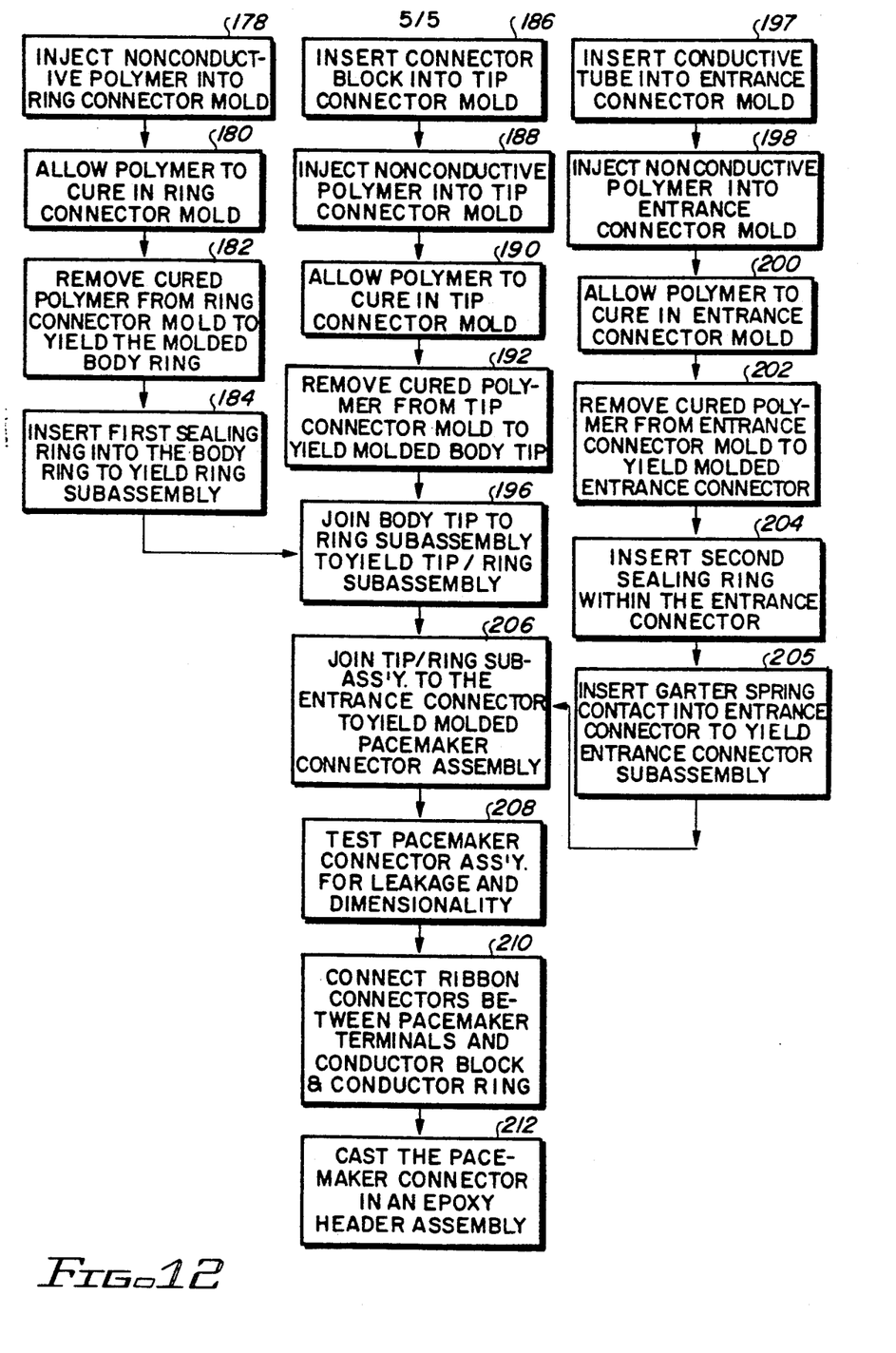
FIG. 12 illustrates the method of making a multi-part molded pacemaker connector in accordance with the present invention.

In FIG. 12, a method of making a molded pacemaker connector 54 in accordance with the present invention is illustrated. The reference numerals in parenthesis are the same as are used in the description of FIGS. 1-11 above. As seen in FIG. 12, the method includes the steps of making three molded pacemaker connector subassemblies (i.e., a ring connector, a tip connector and an entrance connector) and joining them together.

The method steps for making the ring connector subassembly include a first step, at block 178, of injecting a non-conductive polymer into a ring connector mold while the polymer is in a liquid state. A next step, block 180, allows the polymer to cure to assume a solid state. Then, at block 182, the cured polymer is removed from the pacemaker connector mold to yield the molded body ring (66). Next, at block 84, a first inner seal (64) is inserted within the body ring (66) to yield the body ring subassembly (164).

The method steps for making the tip connector include inserting a connector block (74) into a tip connector mold at block 186. Thereafter, a non-conductive polymer is injected into the tip connector mold while the polymer is in a liquid state at block 188. The polymer is then allowed to cure to assume a solid state at block 190, after which the cured polymer, including the connector block (74), is removed from the tip connector mold at block 192. The cured polymer and the connector block (74) molded therein thus comprise the molded body tip 62 of the molded pacemaker connector 54.

The method steps for making the entrance connector subassembly (130) include inserting a conductive tube (124) into the entrance connector mold at block 197. Injecting a non-conductive polymer into the entrance connector mold while the polymer is in a liquid state at block 198. A next step, block 200, allows the polymer to cure to assume a solid state. Then, at block 202, the cured polymer, including the conductive tube (124), is removed from the entrance connector mold to yield the molded entrance connector (70). Next, a second seal is inserted within the molded entrance connector (70) at block 204. At block 205, a garter spring contact (68) is inserted into the molded entrance connector (70) so as to make physical contact with an inner surface of the conductive tube (124). The garter spring contact (68) thus provides a means for making electrical contact between the conductive tube (124) and the outer circumference of the ring electrode (44) of the pacemaker lead 32 inserted into the pacemaker connector 54 so as to pass through the garter spring contact 60.

The method of making the molded pacemaker connector 54 next involves joining the molded body tip 62 to the body ring subassembly (164), including the first seal (64), to produce a tip/ring subassembly at block 196. The method next involves joining the entrance connector subassembly (130), including the second seal (72), the garter spring contact (68) and the conductive tube (124) to the already joined tip/ring subassembly at block 206 to yield the pacemaker connector 54.

Once joined together, the pacemaker connector 54 is tested for leakage conductivity and dimensionality at block 208. If such tests are passed successfully, then the method includes connecting ribbon conductors (174) to respective terminals of a sealed pacemaker at block 210. As a final step, block 212, the method involves casting the tested molded pacemaker connector 54 in an epoxy header assembly 56 onto the sealed pacemaker case 30.

As described above, it is thus seen that the present invention provides a pacemaker connector, and method of making a pacemaker connector, that readily meets the stringent VS-1 standard (or any other standard that may be imposed), and yet is easy and inexpensive to manufacture and assemble, avoiding the necessity of machining individual parts in order to obtain precision dimensions. Advantageously, the pacemaker connector thus provided may be used with pacemaker leads having seals (VS-1B) or with pacemakers not having seals. Further, once assembled, the pacemaker connector can be pretested for leakage, conductivity and dimensionality prior to being cast into a pacemaker header assembly, thereby significantly improving the overall yield of the pacemaker assembly process.

The ease with which the pacemaker connector herein described can be manufactured and assembled is due is large part to the fact that it is made from a plurality of individually molded precision parts. Each individual part advantageously is designed to readily allow the insertion of seals, garter spring contacts, and other connector components, prior to joining the parts together. As also described above, it is seen that the present invention provides a pacemaker connector utilizing a "garter spring contact" to make electrical contact around the entire periphery of a proximal electrode of a pacemaker lead. Such contact assures that a reliable electrical connection will be made and maintained, yet such contact (unlike a set screw) will not damage the proximal electrode. Further, such contact does not require any adjustments (as does a set screw), as the gripping force of the garter spring contact is controlled by the size of the garter spring contact and the dimension (diameter) of the recess within which the garter spring contact resides.

While the invention described herein has been described with reference to specific embodiments and applications thereof, numerous variations and modifications could be made thereto by those skilled in the art without departing from the spirit and scope of the invention as claimed.

What is claimed is:

1. A multi-part pacemaker connector for receiving a proximal end of a pacemaker lead, the pacemaker lead having a first and second spaced-apart electrode, the multi-part pacemaker connector comprising:
    a molded body tip having a recess for receiving the proximal end of the pacemaker lead therein, the body tip including a connector block, the connector block being insert molded so as to form an integral part thereof, the connector block having a channel therethrough, the molded body tip further having a first access window therethrough for making electrical contact with the connector block;
    an electrically conductive garter spring contact;
    a molded entrance connector having a channel therethrough for receiving the proximal end of the pacemaker lead therethrough, the entrance connector including a conductive tube, the conductive tube being insert molded so as to form an integral part thereof, the conductive tube forming a recess for receiving the garter spring contact, the garter spring being sized so as to make circumferential contact with an inner surface of the conductive tube;
    molded body ring having a channel therethrough for receiving the proximal end of the pacemaker lead therethrough, the body ring having a groove for press-fittably receiving the conductive tube, the body ring further having a second access window therethrough for making electrical contact with conductive tube;
    a first joining means for joining the molded body tip to the molded body ring; and
    a second joining means for joining the entrance connector to the body ring;
    whereby the first and second spaced apart proximal electrodes of a pacemaker lead may be inserted into the pacemaker connector and make respective electrical contact with the block electrode and the garter spring contact;
    whereby electrical contact may be made with the first and second proximal electrodes of the pacemaker lead via the first and second access windows, respectively.

2. The multi-part molded pacemaker connector as set forth in claim 1, further comprising:
    an annular inner seal inserted into the molded body ring; and
    an annular entrance seal inserted into the entrance connector;
    wherein the inner and entrance seals having annular ridges for making sealable contact with a proximal end of the pacemaker lead when the first and second proximal electrodes of the pacemaker lead are inserted into the pacemaker connector.

3. The multi-part molded pacemaker connector as set forth in claim 2, wherein the pacemaker connector is sized to comply with VS-1standards.

4. The multi-part molded pacemaker connector as set forth in claim 1, wherein the first joining means comprises:
    first engagement means on one of the body tip or body ring for press-fit engagement with the other of the body tip or body ring.

5. The multi-part molded pacemaker connector as set forth in claim 4, wherein the first engagement means comprises:
    an annular lip protruding from the molded body tip sized for a press-fit within the molded body ring.

6. The multi-part molded pacemaker connector as set forth in claim 1, wherein the second joining means comprises:
    a second engagement means on one of the body ring or the entrance connector for press fit engagement with the other of the body ring or connector entrance.

7. The multi-part molded pacemaker connector as set forth in claim 6, wherein the second engagement means includes a recess in the molded body ring sized for a press-fit with the conductive tube.

8. The multi-part molded pacemaker connector as set forth in claim 1, wherein the molded body tip, the molded body, and the molded entrance connector ring are molded from polysulfone.

9. A pacemaker connector assembly for detachably, electrically connecting first and second spaced-apart electrodes of a proximal end of a pacemaker lead to first and second terminals of an implantable pacemaker, the pacemaker connector assembly comprising:
    a nonconductive entrance connector having a channel therethrough for receiving the proximal end of the pacemaker lead therethrough, the entrance connector further having a conductive tube molded therein;
    a nonconductive body ring having a channel therethrough for receiving the proximal end of the pacemaker lead therethrough, the body ring having a groove for receiving the conductive tube, the body ring including engagement means for joining the entrance connector at one end of the body ring, the body ring further having a first access window therethrough for making electrical contact with the conductive tube;
    a nonconductive body tip having a recess for receiving a proximal end of the pacemaker lead therein, the body tip having a connector block molded therein, the connector block including means for receiving the first electrode of the pacemaker lead, the body tip having a second access window therethrough for making electrical contact with the connector block, the body tip further including an annular lip protruding from the body tip which is sized for a press-fit to the other end of the body ring;

a garter spring contact sized to fit inside the conductive tube, the garter spring contact comprising an electrically conductive material; and means for making respective electrical contact from the connector block and the conductive tube to the first and second pacemaker terminals by way of the first and second access windows, respectively;

whereby the first and second spaced apart electrodes of the pacemaker lead may be inserted into the body tip and body ring so as to make respective electrical contact with the block electrode and the garter spring contact;

whereby electrical contact is made between the first and second electrodes of the pacemaker lead and the first and second pacemaker terminals, respectively.

10. The pacemaker connector assembly as set forth in claim 9, wherein the means for making electrical contact from the connector block and the conductive tube to the first and second pacemaker terminals comprises first and second ribbon conductors.

11. A pacemaker header assembly for detachably, electrically connecting a proximal tip and ring electrode of a proximal end of a pacemaker lead to first and second terminals of an implantable pacemaker, the pacemaker header assembly comprising:

a molded body tip having a recess for receiving the proximal end of the pacemaker lead therein, the body tip including a first conductive means insert molded so as to form an integral part thereof, the first conductive means having means for making electrical contact with the proximal tip electrode;

a molded entrance connector having a channel for receiving the proximal end of the pacemaker lead therethrough, the entrance connector including a second conductive means insert molded so as to form an integral part thereof, the second conductive means having means for making electrical contact with the proximal ring electrode;

a molded body ring having a channel for receiving the proximal end of the pacemaker lead therethrough, the body ring including engagement means for joining the entrance connector to one end of the body ring and for joining the body tip to the other end of the body ring;

means for making electrical contact from the first and second conductive means to the first second pacemaker terminals, respectively; and means for housing the molded body tip, the molded entrance connector, the molded body ring, and the contact means in a biocompatible material.

12. The pacemaker header assembly as set forth in claim 11, wherein the housing means comprises an epoxy casting.

13. The pacemaker header assembly as set forth in claim 11, wherein the body ring includes a recess at one end of the body ring, the body ring further comprising:

an annular inner seal for sealing out bodily fluids, the inner seal being inserted into the recess, the inner seal further having annular ridges for making sealable contact with the proximal end of the pacemaker lead.

14. The pacemaker header assembly as set forth in claim 11, wherein the entrance connector includes a recess at one end of the entrance connector, the entrance connector further comprising:

an annular entrance seal for sealing out bodily fluids, the entrance seal having annular ridges for making sealable contact with the proximal end of the pacemaker lead.

15. The pacemaker header assembly as set forth in claim 11, wherein the means for making electrical contact with the proximal ring electrode comprises:

an electrically conductive garter spring contact inserted inside the second conductive means.

16. A method of making electrical connections between the proximal end of an implantable lead and the electrical circuits within a sealed housing of an implantable medical device, the housing having a first feedthrough terminal therethrough, the method comprising the steps of:

making a first nonconductive connector, the first connector including a cavity therein for receiving a proximal tip electrode of a implantable lead, the first connector further including a conductive terminal for making electrical contact with the proximal tip electrode of the implantable lead;

making a second nonconductive connector, the second connector including a channel for passing the proximal end of the implantable lead therethrough, the second connector further including a first recess;

making a third nonconductive connector, the third connector including a channel for passing the proximal end of the implantable lead therethrough, the third connector further including a second recess;

making a first and a second sealing ring;

inserting the first sealing ring into the first recess of the second connector;

inserting the second sealing ring into the second recess of the third connector;

joining the first, second and third connectors together;

connecting a first conductor at one end to the first feedthrough terminal and at the other end to the conductive terminal, the first, second and third connector, including the conductive terminal, forming a connector subassembly; and casting the connector subassembly in a body compatible material onto the housing.

17. The method of making electrical connections as set forth in claim 16, wherein the step of making a first connector comprises the steps of:

inserting the conductive terminal into a first connector mold;

injecting a nonconductive polymer into the first connector mold while the polymer is in a liquid state, and allowing the polymer to cure to assume a solid state; and removing the first cured polymer, including the conductive terminal, from the first connector mold.

18. The method of making electrical connections as set forth in claim 16, wherein the step of making a second connector comprises the steps of:

injecting a nonconductive polymer into a second connector mold while the polymer is in a liquid state, and allowing the polymer to cure to assume a solid state; and removing the second cured polymer from the second connector mold.

19. The method of making electrical connections as set forth in claim 16, wherein the third connector includes a conductive tube for making electrical contact to a proximal ring electrode of the implantable lead, wherein the step of making a third connector comprises the steps of:
- inserting the conductive tube into a third connector mold;
- injecting a nonconductive polymer into a third connector mold while the polymer is in a liquid state, and allowing the polymer to cure to assume a solid state; and
- removing the third cured polymer, including the conductive tube, from the third connector mold.

20. The method of making electrical connections as set forth in claim 19, wherein the step of making a third connector further comprises the step of:
- inserting a conductive garter spring contact within an inner surface of the conductive tube, the garter spring contact thereby providing electrical contact between the conductive tube and the outer circumference of the proximal ring electrode of the implantable lead when inserted into the connector subassembly.

21. The method of making electrical connections as set forth in claim 19, the housing having a second feedthrough terminal therethrough, wherein the step of making a third connector further comprises the step of:
- connecting a second conductor at one end to the second feedthrough terminal and at the other end to the conductive tube.

22. The method of making electrical connections as set forth in claim 16, further comprising the step of:
- forming an access window into at least two of the body tip, the body ring, or the entrance connector so that the first and second conductors may be connected therethrough.

23. The method of making electrical connections as set forth in claim 16, wherein the step of making a first and a second sealing ring comprises the step of:
- making a first and second annular ring, respectively, from a flexible silicon elastomer, each annular ring having a plurality of circumferential ridges adapted to make sealing contact with the circumference of the proximal end of the implantable lead when inserted into the connector subassembly.

24. The method of making electrical connections as set forth in claim 16, further comprising the step of:
- testing the connector subassembly for leakage, conductivity and dimensionality prior to the casting step.

* * * * *